United States Patent
Moton, Jr. et al.

(10) Patent No.: US 12,240,473 B2
(45) Date of Patent: Mar. 4, 2025

(54) CARRIER TRANSPORT VEHICLE PERSONAL SENSOR ZONE

(71) Applicant: AT&T Intellectual Property I, L.P., Atlanta, GA (US)

(72) Inventors: Robert T. Moton, Jr., Alpharetta, GA (US); Adrianne Binh Luu, Atlanta, GA (US); James Pratt, Round Rock, TX (US); Barrett Kreiner, Woodstock, GA (US); Walter Cooper Chastain, Atlanta, GA (US); Ari Craine, Marietta, GA (US); Robert Koch, Peachtree Corners, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 817 days.

(21) Appl. No.: 17/327,028

(22) Filed: May 21, 2021

(65) Prior Publication Data

US 2022/0371605 A1    Nov. 24, 2022

(51) Int. Cl.
*B60R 16/037* (2006.01)
*A61B 5/00* (2006.01)
(Continued)

(52) U.S. Cl.
CPC ....... *B60W 50/0098* (2013.01); *A61B 5/0077* (2013.01); *A61B 5/6893* (2013.01);
(Continued)

(58) Field of Classification Search
CPC ......... H04W 4/42; H04W 4/48; H04W 48/04; H04L 67/12; G06Q 50/30; G06V 20/597;
(Continued)

(56) References Cited

U.S. PATENT DOCUMENTS 11,333,562 B1 * 5/2022 Johnson ............ G01K 13/20
2008/0114495 A1 * 5/2008 Suyama ............ F24F 11/30
                                                    700/276

(Continued)

FOREIGN PATENT DOCUMENTS

GB          2375389 A   * 11/2002   ............... A61L 9/03

OTHER PUBLICATIONS

"A world of opportunities", NFC Solutions from STMicroelectronics, (May 2021), 36 pages.
(Continued)

*Primary Examiner* — David A Testardi

(57) ABSTRACT

A processing system deployed in a carrier transport vehicle may establish a wireless communication session with a mobile device of a user, assign a zone of the carrier transport vehicle to the user, the zone including a plurality of network-connected devices, obtain a user profile from the mobile device of the user, determine at least one biometric sensor accessible via the mobile device of the user, obtain biometric data of the user from the at least one biometric sensor accessible via the mobile device of the user, determine a condition of the user based upon the biometric data, identify at least one adjustment to at least one of the plurality of network-connected devices in response to the condition of the user that is determined and the user profile, and apply the at least one adjustment to the at least one of the plurality of network-connected devices.

20 Claims, 4 Drawing Sheets

(51) Int. Cl.
  *B60H 1/00* (2006.01)
  *B60N 2/00* (2006.01)
  *B60Q 3/80* (2017.01)
  *B60W 50/00* (2006.01)
  *B64D 11/06* (2006.01)
  *B64D 13/06* (2006.01)
  *H04W 4/021* (2018.01)
  *H04W 4/42* (2018.01)
  *H04W 4/48* (2018.01)

(52) U.S. Cl.
  CPC ..... *B60H 1/00742* (2013.01); *B60H 1/00757* (2013.01); *B60H 1/00785* (2013.01); *B60N 2/0022* (2023.08); *B60Q 3/80* (2017.02); *B60R 16/037* (2013.01); *B64D 11/0646* (2014.12); *B64D 13/06* (2013.01); *H04W 4/021* (2013.01); *H04W 4/42* (2018.02); *H04W 4/48* (2018.02); *B60N 2/0024* (2023.08); *B60N 2/003* (2023.08); *B60N 2210/24* (2023.08); *B60N 2210/40* (2023.08); *B60N 2220/30* (2023.08); *B60N 2230/20* (2023.08); *B60W 2540/21* (2020.02); *B60W 2540/221* (2020.02); *B64D 2013/0655* (2013.01); *B64D 2013/0662* (2013.01); *B64D 2013/0681* (2013.01)

(58) Field of Classification Search
  CPC .. B60R 25/2081; B60R 16/037; B60W 40/08; B60W 50/0098; B60W 2040/0872; B60W 2050/0063–0096; B60H 1/00742; F24F 11/30; B64D 2013/0655
  See application file for complete search history.

(56) References Cited

U.S. PATENT DOCUMENTS

| | | | | |
|---|---|---|---|---|
| 2012/0117094 A1* | 5/2012 | Pratt | ...................... | G06Q 10/06 707/758 |
| 2015/0127215 A1* | 5/2015 | Chatterjee | .......... | B60H 1/00642 701/1 |
| 2016/0089955 A1* | 3/2016 | Ham | .................. | B60H 1/00742 165/202 |
| 2016/0159200 A1* | 6/2016 | Kim | .................... | B60H 1/00971 701/36 |
| 2017/0370604 A1* | 12/2017 | Carey | ...................... | F24F 11/58 |
| 2018/0075717 A1* | 3/2018 | Reinbold | .......... | H04N 21/41265 |
| 2018/0101776 A1* | 4/2018 | Osotio | .................. | G06F 16/258 |
| 2018/0181919 A1* | 6/2018 | Jobling | ................ | G06Q 10/025 |
| 2018/0206725 A1* | 7/2018 | Everett | ................. | A61B 5/1116 |
| 2018/0208017 A1* | 7/2018 | Hernandez | ............ | B60K 37/02 |
| 2018/0222414 A1* | 8/2018 | Ihlenburg | .............. | B60R 16/037 |
| 2018/0229674 A1* | 8/2018 | Heinrich | .................. | A61B 5/18 |
| 2018/0234707 A1* | 8/2018 | Pujia | .................. | H04N 21/4227 |
| 2018/0251122 A1* | 9/2018 | Golston | ................ | B60W 40/08 |
| 2018/0348740 A1* | 12/2018 | Rocci | ...................... | G06V 40/70 |
| 2019/0061957 A1* | 2/2019 | Nicks | ..................... | B64D 13/06 |
| 2019/0126721 A1* | 5/2019 | Salter | ....................... | A61B 5/01 |
| 2019/0176730 A1* | 6/2019 | Choi | .................. | B60H 1/00792 |
| 2019/0196522 A1* | 6/2019 | Bostick | ................ | A61H 33/005 |
| 2019/0239757 A1* | 8/2019 | Berkey | ............ | B64D 11/00155 |
| 2019/0283529 A1* | 9/2019 | Macneille | .......... | B60H 1/00771 |
| 2019/0388794 A1* | 12/2019 | Zavesky | ................. | G06F 3/011 |
| 2020/0172034 A1* | 6/2020 | Rowe | ................ | B60R 16/0237 |
| 2020/0180396 A1* | 6/2020 | Youn | .................. | B60H 1/00821 |
| 2020/0189352 A1* | 6/2020 | Han | .................. | B60H 1/00285 |
| 2020/0216093 A1* | 7/2020 | Lee | ......................... | G06V 40/70 |
| 2020/0331320 A1* | 10/2020 | Saeki | .................. | B60H 1/00971 |
| 2021/0031786 A1* | 2/2021 | Gallagher | ............ | B60N 2/0244 |
| 2021/0107334 A1* | 4/2021 | Shtrom | ................ | B60H 1/0073 |
| 2021/0260958 A1* | 8/2021 | Nilsson | ..................... | G01K 3/06 |
| 2021/0262680 A1* | 8/2021 | Zhao | ........................ | F24F 11/57 |
| 2021/0282472 A1* | 9/2021 | Gueritee | .............. | A61B 5/6802 |
| 2021/0394912 A1* | 12/2021 | Krenz | ...................... | B64D 13/00 |
| 2022/0189227 A1* | 6/2022 | Purohit | .................... | G07C 9/22 |
| 2022/0289211 A1* | 9/2022 | Dadam | ................... | F01N 1/065 |
| 2022/0291680 A1* | 9/2022 | Schwindt | ............... | B64D 45/00 |
| 2022/0341788 A1* | 10/2022 | Seoane | .................. | G06V 20/59 |

OTHER PUBLICATIONS

Asma Ahmad Farhan, et al., "Predicting Individual Thermal Comfort using Machine Learning Algorithms", downloaded from https://nlab.engr.uconn.edu/papers/Farhan-CASE2015.pdf, on Mar. 18, 2021, 6 pages.

Wooyoung Jung, et al., "Heat Flux Sensing for Machine-Learning-Based Personal Thermal Comfort Modeling", Aug. 25, 2019, 22 pages, downloaded from https://www.ncbi.nlm.nih.gov/pmc/articles/PMC6749310/pdf/sensors-19-03691.pdf.

* cited by examiner

CARRIER TRANSPORT VEHICLE PERSONAL SENSOR ZONE

The present disclosure relates generally to carrier transport vehicles and more particularly to apparatuses, computer-readable storage devices, and methods for identifying at least one adjustment to at least one of a plurality of network-connected devices of a carrier transport vehicle in response to a condition of a user that is determined based upon biometric data obtained from at least one biometric sensor accessible via a mobile device of the user and a user profile.

BACKGROUND

Despite passenger air travel being ubiquitous for decades, many passengers still (or increasing) perceive the experience as stressful and anxiety-inducing, rather than as part of an enjoyable trip. For instance, current procedures of many airlines, as well as governmental regulations, may confine passengers to their seats for long periods of time. In addition, in many cases, the personal space afforded to passengers has been increasingly reduced. At the same time, many passengers may experience discomfort relating to being too hot, or more often too cold, the air being too damp, or more often too dry for the passengers' preferences, and so on. Passengers of other carrier transport vehicles, such as trains, buses, ferries, and so forth, may experience similar discomforts, contributing to a negative perception of an overall journey.

SUMMARY

In one example, the present disclosure describes an apparatus, non-transitory computer-readable storage device, and method for identifying at least one adjustment to at least one of a plurality of network-connected devices of a carrier transport vehicle in response to a condition of a user that is determined based upon biometric data obtained from at least one biometric sensor accessible via a mobile device of the user and a user profile. For instance, in one example, a processing system including at least one processor deployed in a carrier transport vehicle may establish a wireless communication session with a mobile device of a user, assign a zone of the carrier transport vehicle to the user, the zone including a plurality of network-connected devices, obtain a user profile from the mobile device of the user, and determine at least one biometric sensor accessible via the mobile device of the user. The processing system may next obtain biometric data of the user from the at least one biometric sensor accessible via the mobile device of the user, determine a condition of the user based upon the biometric data, and identify at least one adjustment to at least one of the plurality of network-connected devices in response to the condition of the user that is determined and the user profile. The processing system may then apply the at least one adjustment to the at least one of the plurality of network-connected devices.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
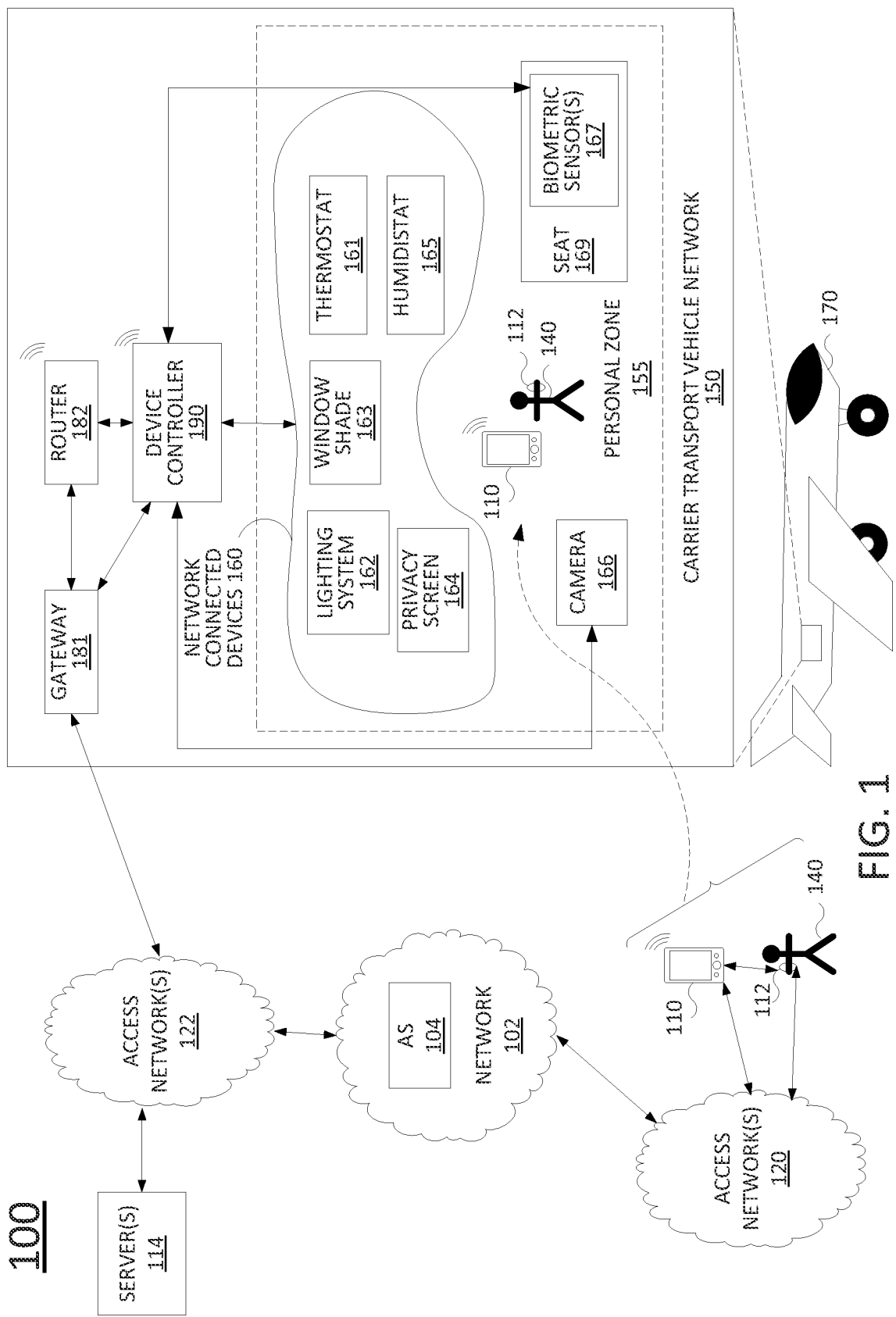
FIG. 1 illustrates an example system comprising one or more communication networks related to the present disclosure.

Despite passenger air travel being ubiquitous for decades, many passengers still (or increasing) perceive the experience as stressful and anxiety-inducing, rather than as part of an enjoyable trip. For instance, current procedures of many airlines, as well as governmental regulations, may confine passengers to their seats for long periods of time. In addition, in many cases, the personal space afforded to passengers has been increasingly reduced. At the same time, many passengers may experience discomfort relating to being too hot, or more often too cold, the air being too damp, or more often too dry for the passengers' preferences, and so on. Passengers of other carrier transport vehicles, such as trains, buses, ferries, and so forth, may experience similar discomforts, contributing to a negative perception of an overall journey.

In one example, the present disclosure obtains biometric data characterizing a user's physical condition from biometric sensors of the user and/or of a carrier transport vehicle, as well as environmental conditions in a zone of the carrier transport vehicle. In addition, the present disclosure may then control one or more network-connected devices to adjust one or more aspects of the environmental conditions to achieve a change in the user's condition, e.g., when the user is seated for an extended period of time. When a user is seated for a relatively short period of time in a location, the user may temporarily adapt to, or perhaps enjoy, whatever the physical environment around the location presents. However, if the user is predicted to be seated for an extended period of time, the user may wish to have a greater degree of control of the environment than currently exists. For instance, examples of the present disclosure may provide a solution for users who are seated on an airplane or other carrier transport vehicles, perhaps for hours. However, examples of the present disclosure may also relate to other similar situations, such as being seated in a theater, concert, sporting event, or the like, where a personal zone comprising various network-connected devices may be assigned to a user.

The user, e.g., a passenger of a carrier transport vehicle, may be equipped with a mobile device, such as a smartphone. The device may include near-field and wide area networking capabilities and may include sensors, such as a camera, microphone, thermostat, Global Positioning System (GPS) unit and/or other location awareness, motion sensors, e.g., a gyroscope, compass, accelerometer, and others. The mobile device may comprise or may be in communication with a wearable computing device, such as a smartwatch, and may include biometric sensors such as a heart rate monitor, electrocardiograph (EKG), pulse oximeter, and the like. The mobile device may also have software installed and executed thereon to enable the mobile device to interpret the sensor data, such as to perform facial recognition, speech recognition, mood detection, health detection, such as blood pressure and stress level, and other user conditions. In one example, the user's mobile device may have installed thereon a personal environmental control application (app), which in one example may be a part of, or in communication with, a virtual assistant app of the mobile device.

The personal environmental control app may use data accessible on the mobile device, such as calendar information, or data collected or derived from sensors on the device, such as location information, motion detection, posture detection, or data from another app on the mobile device, such as airplane boarding data from an airline app or an event ticketing app, to determine that the user is in an environment where it is expected that the user will be seated for an extended period of time. For instance, the personal environmental control app may combine data from multiple sources to determine that the user is on a plane and seated, for example. In one example, the personal environmental control app may maintain a user profile of the user that may include preferences and tolerance ranges for a variety of environmental conditions. In one example, the user profile may include a thermal preference model of the user. For instance, such a thermal preference model may comprise a machine learning model that adapts to a user over time and is based upon biometric data of the user (e.g., skin temperature of hands and/or face), environmental data (e.g., temperature, wind speed, etc.), quantity of clothing, and feedback data (e.g., user input indicating whether the user feels cold, very cold, hot, very hot, or comfortable, or feedback from other biometric data, e.g., a user mood determined via a different model or models for detecting mood(s) from user biometric data). Thus, in one example a network-based database associated with the personal environmental control app may also store historical data for the user and user preferences that may be used to save personal environment control settings. In one example, when the personal environmental control app predicts that the user is seated, the personal environmental control app may optionally prompt the user to invoke the capabilities of the personal environmental control app.

In one example, in response to obtaining the user's opt-in to environmental control, the personal environmental control app may determine what sensors are available to collect data regarding the user's environment. The available sensors may be included on the user's device or may be external to the device and may be shared sensors—that is, not owned by the user, but perhaps owned by an airline, in this case. Available sensors on the device may include a microphone, camera, thermostat, biometric sensors, motion sensors, location sensor, and others. Available shared sensors may include cameras, motion sensors, heat sensors, air flow sensors, microphones, and others.

Sensor data may be collected from all of the available sensors and in one example may be presented via a user interface (UI) of the personal environmental control app to the user. In addition, the sensor data may be processed to calculate additional metrics. For instance, current heart rate data may be compared against historical heart rate data of a user to estimate a current stress level. Likewise, camera image or video data may be processed to calculate a density of people within the environment or a distance of the user to the nearest other person. A microphone may sense noise, but a speech recognition software may interpret the noise as containing human speech.

The personal environmental control app may determine what personal environment controls are available to the user. This may be accomplished by the personal environmental control app causing the device to search for nearby environmental control devices (e.g., "network connected devices") that broadcast their availability. These control devices may broadcast their availability via Wi-Fi, Bluetooth, or other near-field technologies. Alternatively, the user's device may send a query to a database of environmental control devices, which may return a list of available environmental control devices based on the user's location. The available environmental control devices and their capabilities for controlling the user's personal environment may be presented to the user via a UI. For example, the UI may provide a display of a plurality of environmental control devices' availabilities and for each such device, an option for the user to use it or not. If the user opts to use an environmental control device, the UI may present setting levels or other control options for the user. It should be noted that as referred to herein, environmental control devices may include sensors, such as a thermostat which includes a temperature sensor that is used to maintain or achieve a particular temperature setting. However, other environmental control devices may not include sensors, such as privacy screens, which affect the environment without necessarily collecting data from the environment.

It should be noted that in accordance with the present disclosure, the user's personal environment is the user's immediate proximate environment and has limited effect on the personal environments of other users nearby. To illustrate, the UI may present a slider bar, menu, or the like with options to affect controls related to sound in the user's personal environment. This may be presented, for instance, if the personal environmental control app detects one or more controllable speakers. More specifically, the speaker(s) may be directional speakers that direct output audio only in the direction of the user's head. For instance, the user's head location may be determined if the personal environmental control app detects an available camera and the user permits the user's head location to be tracked via processing of the captured video and/or images. The head location may be determined periodically and sent, via the personal environmental control app, to the directional speaker(s) to permit the speaker(s) to determine the correct direction to send audio output and adjust as needed.

The user may, for example, set the sound controls to cancel ambient sounds. In this case, a microphone sensor may capture ambient noise and the personal environmental control app may create one or more noise signals to cancel the ambient noise and send the signal(s) to the directional speaker(s) to play. Similarly, the user may instruct the directional speaker(s) to play white noise, music, audio for a movie or other videos, audio for a phone conversation or video conversation, or other audios. The audio source may be from the user's device or from another source accessible via a network-based or a peer-to-peer communication. In this way, the user's immediate sound environment is controlled without a need for headphones. In one example, the user may also mute the airplane's public address system, which disables any non-emergency and non-mandated flight announcements from being played over the user's directional speaker. The user may optionally choose to share the user's personal sound environment settings (and other settings) with flight attendants, for example presented on a display UI for flight crew.

Similarly, if the personal environmental control app identifies sensors related to ambient air quality and temperature, the user may also be presented with a UI to control ambient air in their environment. For instance, the user may control the temperature of air flowing into their seating area. Alternatively, or in addition, if a contagion sensor or air quality sensor detects poor air conditions, the user may adjust a controllable overhead fan to a higher setting. Alternatively, this may be done without requiring user interaction. Such detection may be noted in a log and sent to a server to create a record of maintenance needed, such as replacing a filter at that seat.

Likewise, if the personal environmental control app detects available controls to adjust seat comfort settings, it may present a set of control options via the personal environmental control app UI. If the personal environmental control app detects available controls to adjust the user's surrounding field of view, it may present a set of field of view controls to the user. For instance, the user's seat may include a controllable privacy wall which the user may select to deploy or retract into place. In one example, the seat may include display screen which may be used for video content display, or which may be used to present an expanded window view, such that the video feed from a camera on the exterior of the carrier transport vehicle may be displayed. In this way, a simulation of the complete wall section next to the user may be presented as if the window was expanded to include a larger area, or the entire section of wall in the user's immediate environment. In a similar manner, such a display may be deployed for a non-window seat, so as to simulate that the user is seated by a window when the user is not.

By detecting or predicting that the user is expected to be seated for an extended period of time, the system may identify an opportunity to provide services to the user that are optimized for longer durations of time, such as hours. For instance, some health studies may yield improved data for diagnoses if done over a period of time. Accordingly, in one example, with the opt-in and permission of the user, sensors on the user's device(s) and/or shared sensors may be used to collect data, which may be sent by the user's device and/or an on-board processing system of the carrier transport vehicle to another computing system for analysis, such as a computing system of an entity conducting one or more health studies. For instance, seat sensors, cameras, motion sensors, body temperature sensors, and others may be used to gather data needed for health studies. For instance, video may be analyzed to identify breathing patterns and pauses in breathing, as for a possible sleep apnea diagnosis or for inclusion in a reference population data set. These and other aspects of the present disclosure are described in greater detail below in connection with the examples of FIGS. 1-4.

To further aid in understanding the present disclosure, FIG. 1 illustrates an example system 100 in which examples of the present disclosure may operate. The system 100 may include any one or more types of communication networks, such as a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, 4G, 5G and the like), a long term evolution (LTE) network, and the like, related to the current disclosure. It should be noted that an IP network is broadly defined as a network that uses Internet Protocol to exchange data packets. Additional example IP networks include Voice over IP (VoIP) networks, Service over IP (SoIP) networks, and the like.

In one example, the system 100 may comprise a network 102 (e.g., a telecommunication network of a telecommunication service provider). The network 102 may be in communication with one or more access networks 120 and 122, and the Internet (not shown). In one example, network 102 may combine core network components of a cellular network with components of a triple play service network; where triple-play services include telephone services, Internet services and television services to subscribers. For example, network 102 may functionally comprise a fixed mobile convergence (FMC) network, e.g., an IP Multimedia Subsystem (IMS) network. In addition, network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Network 102 may further comprise a broadcast television network, e.g., a traditional cable provider network or an Internet Protocol Television (IPTV) network, as well as an Internet Service Provider (ISP) network. In one example, network 102 may include a plurality of television (TV) servers (e.g., a broadcast server, a cable head-end), a plurality of content servers, an advertising server (AS), an interactive TV/video-on-demand (VoD) server, and so forth. For ease of illustration, various additional elements of network 102 are omitted from FIG. 1.

In one example, the access networks 120 and 122 may comprise Digital Subscriber Line (DSL) networks, public switched telephone network (PSTN) access networks, broadband cable access networks, Local Area Networks (LANs), wireless access networks (e.g., an Institute of Electrical and Electronics Engineers (IEEE) 802.11/Wi-Fi network and the like), cellular access networks, $3^{rd}$ party networks, and the like. For example, the operator of network 102 may provide a broadband Internet access service, or any other types of telecommunication service to subscribers via access networks 120 and 122. In one example, the access networks 120 and 122 may comprise different types of access networks, may comprise the same type of access network, or some access networks may be the same type of access network and other may be different types of access networks. In one example, the network 102 may be operated by a telecommunication network service provider. The network 102 and the access networks 120 and 122 may be operated by different service providers, the same service provider or a combination thereof, or may be operated by entities having core businesses that are not related to telecommunications services, e.g., corporate, governmental, or educational institution LANs, and the like.

In one example, the access networks 120 may be in communication with one or more devices, e.g., device(s) 110 and biometric sensor(s) 112. Similarly, access networks 122 may be in communication with various devices or computing systems, e.g., server(s) 114, gateway 181, and/or devices in carrier transport vehicle network 150 that are accessible via gateway 181. Access networks 120 and 122 may transmit and receive communications between device 110 and biometric sensor(s) 112, servers 114, devices in carrier transport vehicle network 150, application server (AS) 104 and/or other components of network 102, devices reachable via the Internet in general, and so forth. In one example, device 110 may comprise any subscriber/customer endpoint device configured for wireless communication such as a laptop computer, a Wi-Fi device, a Personal Digital Assistant (PDA), a mobile phone, a smartphone, an email device, a computing tablet, a messaging device, and the like. In one example, device 110 may have both cellular and non-cellular access capabilities and may further have wired communication and networking capabilities. In one example, device 110 may be associated with a user 140 (e.g., a passenger) who may book a trip with a carrier (e.g., reserve a passenger seat, space, or other accommodations) such as via aircraft 170 (e.g., a type of carrier transport vehicle). For instance, device 110 may have a carrier app installed thereon, which may facilitate booking/reserving transport of passengers and/or luggage items by carrier transport vehicles scheduled for various routes.

In one example, user 140 may further have one or more biometric sensor(s) 112, e.g., a wearable device, that may be in communication with device 110, e.g., via a wired or a wireless connection, such as via an infrared transmitter or transceiver, a transceiver for Institute for Electrical and Electronics Engineers (IEEE) 802.11 based communications (e.g., "Wi-Fi"), IEEE 802.15 based communications (e.g., "Bluetooth", "ZigBee", etc.), and so forth. Alternatively, or in addition, biometric sensor(s) 112 may connect to various networks independently of a respective mobile device. The biometric sensor(s) 112 may comprise: a heart rate monitor, an electrocardiogram device, an acoustic sensor, a sensor for measuring a breathing rate of user 140, a galvanic skin response (GSR) device, and so forth.

In one example, the biometric sensor(s) 112 may measure or capture data regarding various physical parameters of a user (broadly, "biometric data") from which a mood, e.g., a mental or emotional state, may be calculated. For instance, the biometric sensor(s) 112 may record for user 140: a heart rate, a breathing rate, a skin conductance and/or sweat/skin moisture level, a temperature, a blood pressure, a voice pitch and tone, body movements, e.g., eye movements, hand movements, and so forth. In another example, the biometric sensor(s) 112 may measure brain activity, e.g., electrical activity, optical activity, chemical activity, etc., depending upon the type(s) of biometric sensor(s).

In one example, data gathered by biometric sensor(s) 112 may be used to calculate or determine a mood of user 140. In addition, relevant biometric data for user 140 may also be gathered from other devices, such as camera 166 and/or biometric sensors 167 of seat 169, and so forth, as described in greater detail below. For example, camera 166 may capture images or video comprising facial image data of user 140, and/or an attached or integrated microphone may record voice(s) within recording range of the microphone. Similarly, device 110, biometric sensor(s) 112, and/or biometric sensors 167 (e.g., including at least a microphone/acoustic sensor) may record audio data of a voice of user 140 from which pitch, tone, and other parameters may be calculated. Alternatively, or in addition, words and phrases in the audio data may also be determined, e.g., using speech recognition techniques. In another example, a posture of user 140 may be measured from captured images and/or video of camera 166 and/or from biometric sensors 167 of seat 169. For instance, a slouching posture may be associated with depression or sadness, while sitting or standing straight is more correlated with happiness or contentment. In still another example, device 110 may record the physical forces that are applied on a touchscreen as the user interacts with the touchscreen, and so forth.

In the example of FIG. 1, aircraft 170 comprises a gateway 181, e.g., for external communications via access networks 122, network 102, and so forth. For instance, access networks 122 may include a cellular access network, e.g., an evolved Universal Terrestrial Radio Access Network (eUTRAN) comprising one or more eNodeBs and/or a 5G network comprising gNBs, or the like. In one example, the communication between gateway 181 and the access networks 122 may comprise a Long Term Evolution (LTE) machine type communication (MTC). For instance, LTE-MTC is part of 3GPP Release 13 and provides specifications for multiplexing low bandwidth and/or delay tolerant communications for devices in potentially poor coverage conditions, e.g., over long distances, in indoor or below-grade environments, and so on, with high bandwidth 4G and beyond mobile data. Alternatively or in addition, gateway 181 may communicate with the access networks 122 via Narrowband Internet of Things (NB-IoT) other low power wide area network (LPWAN) radio technologies, or any other cellular or non-cellular wireless communication modalities.

As further illustrated in FIG. 1, gateway 181 may be in communication with a router 182, which may be capable of both wired and/or wireless communication. In turn, router 182 may receive data from and send data to the appropriate devices, e.g., device 110, biometric sensor(s) 112, camera 166, biometric sensors 167, or various other network connected devices 160, which may include thermostat 161, lighting system 162, window shade 163, privacy screen 164, humidistat 165, and so forth. In one example, router 182 may comprise a wired Ethernet router and/or an IEEE 802.11 (Wi-Fi) router, and may communicate with respective devices in carrier transport vehicle network 150 via wired and/or wireless connections. The carrier transport vehicle network 150 also includes device controller 190, which may be capable of both wired and/or wireless communication and which may communicate with device 110, biometric sensor(s) 112, camera 166, biometric sensors 167, or various other network connected devices 160 via router 182 and/or directly (e.g., peer-to-peer communications without passing via router 182 or via any other intermediate devices). For instance, each of these devices may include a transceiver and/or other components for peer-to-peer and/or short range wireless communications, e.g., IEEE 802.11 based communications (e.g., Wi-Fi, Wi-Fi Direct), IEEE 802.15 based communications (e.g., Bluetooth, Bluetooth Low Energy (BLE), and/or ZigBee communications), LTE Direct, Dedicated Short Range Communications (DSRC), e.g., in the 5.9 MHz band, or the like, for wired communications (e.g., for wired Ethernet or the like), and so forth. The biometric sensors 167 may comprise the same or similar biometric sensors as biometric sensor(s) 112, such as a thermal sensor, a pulse oximeter, a skin conductance sensor, a blood pressure meter, a microphone, a pressure sensor (e.g., to detect pressure at various portions of seat 169), and so forth. In one example, one or more of the biometric sensors 167 may be deployed in an armrest of seat 169. For instance, user 140 may place an arm on the armrest, which may then allow biometric sensors 167 to measure and collect various biometric data of the user 140.

Figure 3:
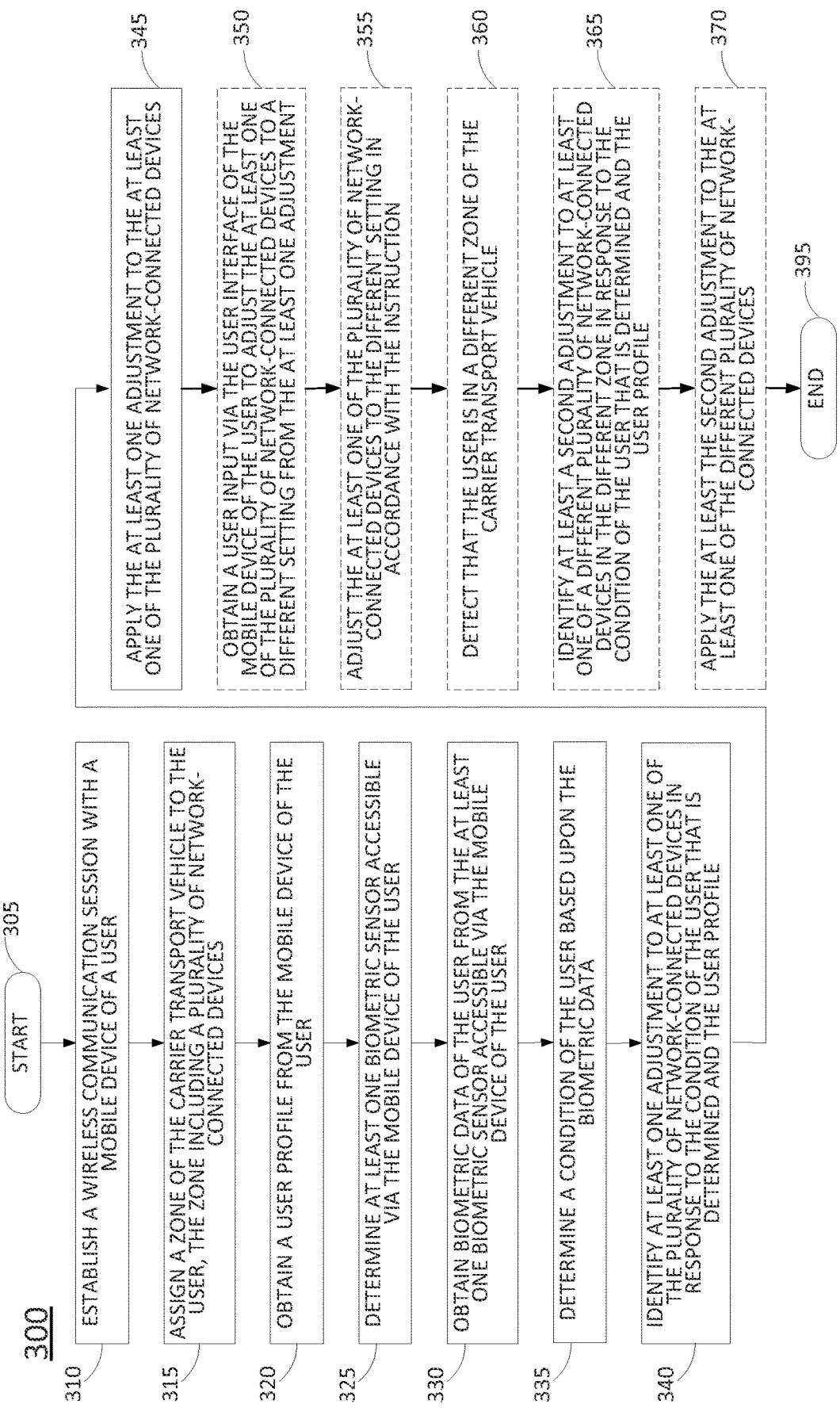
FIG. 3 illustrates a flowchart of an example method for identifying at least one adjustment to at least one of a plurality of network-connected devices of a carrier transport vehicle in response to a condition of a user that is determined based upon biometric data obtained from at least one biometric sensor accessible via a mobile device of the user and a user profile.
Figure 4:
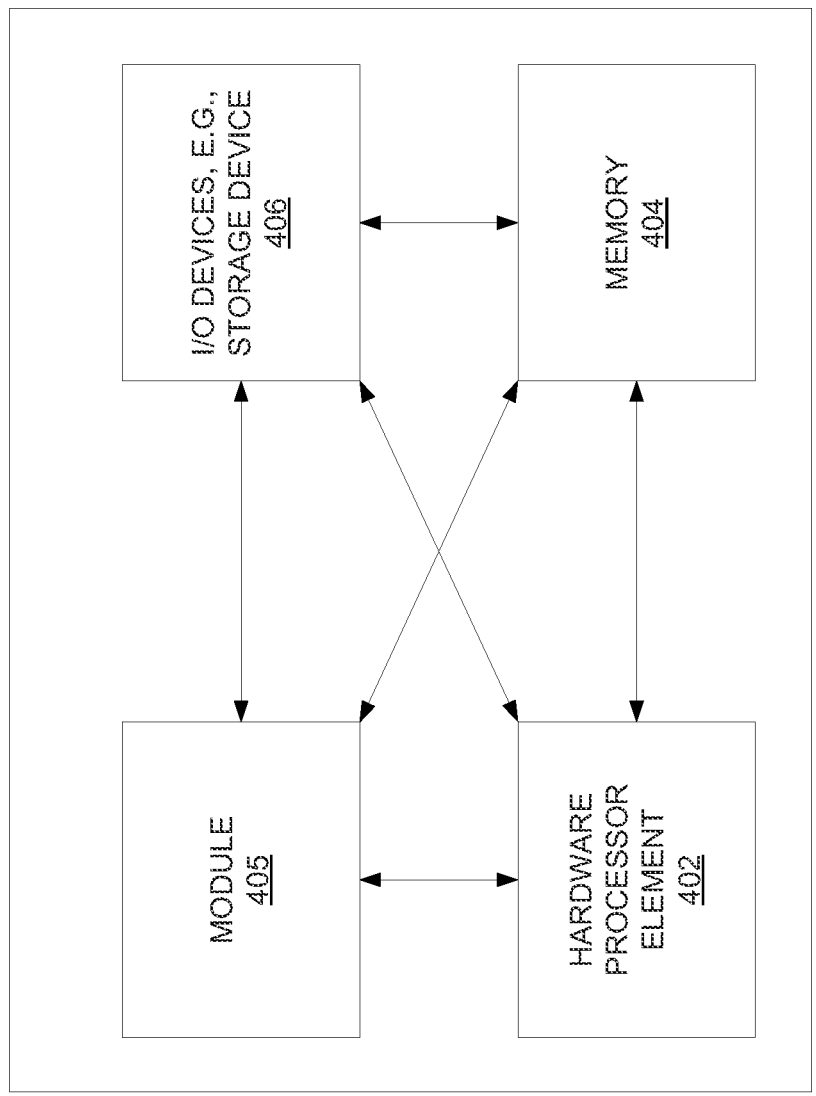
FIG. 4 illustrates a high level block diagram of a computing device specifically programmed to perform the steps, functions, blocks and/or operations described herein.

In one example, device controller 190 may comprise a computing device or processing system, such as computing system 400 depicted in FIG. 4, and may be configured to perform one or more operations or functions for identifying at least one adjustment to at least one of a plurality of network-connected devices of a carrier transport vehicle in response to a condition of a user that is determined based upon biometric data obtained from at least one biometric sensor accessible via a mobile device of the user and a user profile. A flowchart of an example method 300 for identifying at least one adjustment to at least one of a plurality of network-connected devices of a carrier transport vehicle in response to a condition of a user that is determined based upon biometric data obtained from at least one biometric sensor accessible via a mobile device of the user and a user profile is illustrated in FIG. 3 and discussed in greater detail below.

In addition, it should be noted that as used herein, the terms "configure," and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device, or computing system, including one or more processors, or cores (e.g., as illustrated in FIG. 4 and discussed below) or multiple computing devices collectively configured to perform various steps, functions, and/or operations in accordance with the present disclosure.

In one example, server(s) 114 may each comprise a computing system or server, such as computing system 400 depicted in FIG. 4, and may be configured to perform operations in connection with examples of the present disclosure for identifying at least one adjustment to at least one of a plurality of network-connected devices of a carrier transport vehicle in response to a condition of a user that is determined based upon biometric data obtained from at least one biometric sensor accessible via a mobile device of the user and a user profile, e.g., as described in connection with FIG. 3. For instance, server(s) 114 may provide a connected device management system for carrier transport vehicle networks in accordance with the present disclosure. In one example, server(s) 114 may represent one or more distributed file systems, e.g., a Hadoop® Distributed File System (HDFS™), or the like. Server(s) 114 may receive and store user profile information regarding users/passengers, such as user 140, as described in greater detail below.

In one example, AS 104 may comprise a network-based server (or servers) providing a connected device management system for carrier transport vehicle networks. In this regard, AS 104 may comprise the same or similar components as those of server(s) 114 and may provide the same or similar functions, or at least a portion thereof. For instance, an operator of network 102 may provide a connected device management service for carrier transport vehicle networks via AS 104 in accordance with the present disclosure (e.g., in addition to telecommunication services such as TV, phone, internet access, etc., as described above). For example, AS 104 may store and update user profiles as described herein. In one example, AS 104 may also provide such data to an airline or other carriers in connection with particular trips of the user 140. For instance, when user 140 books a trip with a carrier associated with aircraft 170, AS 104 may provide profile information of the user profile to server(s) 114 and/or to aircraft 170.

In an illustrative example, device controller 190 may detect the presence of user 140 in a personal zone 155 of the aircraft 170 containing at least one network-connected device (e.g., network connected devices 160, camera 166 and/or biometric sensors 167). In one example, device controller 190 may then obtain a user profile of user 140 with respect to the at least one network-connected device and/or at least one environmental condition. In one example, the user profile may be obtained from the device 110. For instance, device 110 may broadcast the user profile, e.g., via IEEE 802.11-based broadcast, for IEEE 802.15-based broadcast, or the like, which may be received by device controller 190. In another example, a network-based processing system, e.g., server(s) 114 may store and/or transmit the user profile. For instance, device controller 190 may detect the presence of user 140, e.g., by detecting device 110 and/or biometric sensor(s) 112, and may then request the user profile from server(s) 114. In still another example, the user profile may be obtained from device 110 and/or server(s) 114 in advance of the travel of user 140 on-board aircraft 170. For instance, the user 140 may cause the user profile to be uploaded to a carrier's server(s) (e.g., server(s) 114) which may transmit the user profile to device controller 190 via gateway 181, e.g., when the aircraft 170 is stopped at an airport. As noted above, in one example, the user profile may include preferences and tolerance ranges of the user regarding a plurality of environmental conditions.

In addition, the device controller 190 may determine available biometric sensors that are accessible via the user device 110 and/or biometric sensor(s) 112. In one example, the user profile may include permission(s) of user 140 with respect to the biometric data that may be gathered via biometric sensor(s) 112 and/or biometric sensors of device 110. For instance, the user 140 may be willing to share skin temperature data with device controller 190, but may not allow EKG data to be accessed by device controller 190. In one example, the user profile may also provide instructions to allow device controller 190 access to the biometric data, e.g., regarding formatting, access tokens, frequency of data collection and/or transmission, etc.

In one example, device controller 190 may select at least one initial setting for at least one of the network-connected devices 160 in accordance with the user profile. For instance, device controller 190 may select settings at the midpoints of various ranges for the user's preferences, however, subject to any maximums and minimums imposed by the operator of aircraft 170. For instance, a setting for window shade 163 may be required to be "full open" until a cruising altitude is reached. Similarly, the seat recline may be required to be upright until such a cruising altitude is reached. In one example, the temperature may have a maximum setting of 75 degrees. Thus, if the preference of user 140 for temperature is 78-82 degrees, but the tolerance range is 68-90, the device controller 190 may adjust the thermostat setting to 75 degrees. It should be noted that in one example, if the maximum-minimum range as selected by the operator of aircraft 170 is not within the tolerance range of the user 140, then the maximum-minimum range may still not be exceeded, but this condition may be noted as an input to one or more machine learning models for detecting a mood of user 140. For instance, the fact that a setting is outside of the user's stated tolerance range may be impactful as to whether or not the user is experiencing one or more negative moods, such as being anxious, nervous, upset, frightened, annoyed, angry, etc.

Continuing with the present example, once the device controller 190 selects/adjusts initial settings of network connected devices 160, the device controller 190 may then continue to gather biometric data of the user 140 and environmental data regarding personal zone 155, and may continue to adjust various settings of the network connected devices 160 in response. To illustrate, other passengers nearby the personal zone 155 of user 140 may engage in conversation which may exceed a noise preference level of the user. This may be detected, for example, by device controller 190 collecting data via a microphone of device 110 and/or one of biometric sensors 167. As such, device controller 190 may raise a privacy screen 164, may apply noise cancellation via one or more directional speakers (not shown), and so forth.

In one example, the user profile may include a thermal preference model of the user 140. For instance, such a thermal preference model may comprise a machine learning model that adapts to user 140 over time and is based upon biometric data of the user 140 (e.g., skin temperature of hands and/or face), environmental data (e.g., temperature, wind speed, etc.), quantity of clothing, and feedback data (e.g., user input indicating whether the user feels cold, very cold, hot, very hot, or comfortable, or feedback from other biometric data, e.g., a user mood determined via a different model or models for detecting mood(s) from user biometric data). In any case, device controller 190 may collect biometric data of user 140 (e.g., skin temperature) and environmental data (e.g., temperature, and in one example wind speed), which may be input to the machine learning model, which may output an indication of whether the user feels cold, hot, or is comfortable. In addition, device controller 190 may then adjust thermostat 161 up or down depending upon if the user is detected to be cold or hot. It should be noted that the thermal preference of the user is not directly dependent upon either the external temperature or the temperature of the user 140, but is a complex interaction between these and other factors, including a mood of user 140, a time of day, when the user 140 has last eaten, what the user 140 has had to drink, when the user 140 has last had the opportunity to use a restroom, etc., which is learned by the machine learning model.

In this regard, it should be noted that as referred to herein, a machine learning model (MLM) (or machine learning-based model) may comprise a machine learning algorithm (MLA) that has been "trained" or configured in accordance with input data (e.g., training data) to perform a particular service, e.g., to detect a perceived thermal state of a user, or a value indicative of such a perceived thermal state (or to detect one or more moods from among a variety of possible quantifiable moods, a described in greater detail below). Thus, in other examples, the present disclosure may incorporate various types of MLAs/models that utilize training data, such as a support vector machine (SVM), e.g., a linear or non-linear binary classifier, a multi-class classifier, a deep learning algorithm/model, such as another type of deep learning neural network or deep neural network (DNN), a generative adversarial network (GAN), a decision tree algorithms/models, such as gradient boosted decision tree (GBDT), a k-nearest neighbor (KNN) clustering algorithm/model, and so forth. In one example, the MLA may incorporate an exponential smoothing algorithm (such as double exponential smoothing, triple exponential smoothing, e.g., Holt-Winters smoothing, and so forth), reinforcement learning (e.g., using positive and negative examples after deployment as a MLM), and so forth.

Similarly, in one example, device controller 190 may collect biometric data of user 140 and perform mood detection in accordance with the biometric data. For example, the device controller 190 may quantify a mood (or moods) of user 140 based upon the biometric data. In one example, moods may include a defined set of positive moods/mental states such as, happy, excited, relaxed, content, calm, cheerful, optimistic, pleased, blissful, amused, refreshed, or satisfied; negative moods such as, sad, angry, upset, devastated, mad, hurt, sulking, depressed, annoyed, or enraged; and neutral moods such as indifferent, bored, sleepy, and so on.

These moods are only examples and are not to be interpreted as limitations of the present disclosure. In one example, different moods may have different signatures or profiles to which biometric data that is gathered from various biometric sensors, e.g., biometric sensor(s) 112, biometric sensors 167, camera 166, etc., or to which data derived from the biometric data may be compared in order to determine a most likely current mood for user 140. The signatures may be based upon various types of biometric data, e.g., depending upon the types of the biometric sensor(s) 112 and/or biometric sensors 167 that are in use and the types of biometric data that the biometric sensor(s) 112 and/or biometric sensors 167 collect, and so forth.

For example, if the biometric data for user 140 includes facial image data gathered from camera 166, the device controller 190 may calculate the mental state of user 140, at least in part, using pattern matching, e.g., to eigenfaces of user 140 based upon a training data set, or composite eigenfaces representative of various mental states/moods over a training data set from faces of various users and for different mental states/moods. For instance, such eigenfaces may be obtained as part of the user profile as discussed above.

An eigenface may comprise a quantized vector of a face of user 140. In accordance with the present disclosure, different eigenfaces may be learned that are representative of user 140 in different moods. In one example, these eigenfaces may extracted during an offline training phase. Accordingly, an eigenvector/eigenface-based algorithm may then be used to determine facial similarity (and hence a mood of user 140). Utilizing this algorithm, a single feature space (basis) is constructed from a large set of training facial data obtained off-line (labeled with respective moods). Thus, in accordance with the present disclosure, the facial image data gathered from camera 166 may be projected into the known basis to generate smaller dimensional features (e.g., a quantized vector). The device controller 190 may then calculate the Euclidean distance between the quantized vector of the facial image data gathered from camera 166 and the eigenfaces of the user 140 representing different moods to determine the best match (e.g., the shortest distance). It should be noted that although the use of eigenfaces is described, the present disclosure is not limited to the use of this technique. For example, the set of quantized vectors may be encoded using techniques such as principal component analysis (PCA), partial least squares (PLS), sparse coding, vector quantization (VQ), deep neural network encoding, and so forth.

In another example, device controller 190 may calculate a mood of user 140 from audio data gathered via device 110, one of the biometric sensors 167, biometric sensor(s) 112, and/or other devices in the personal zone 155 of user 140. For instance, the audio data may be compared to various signatures or profiles for different moods, and a best matching mood may be calculated as the current mood for the user 140. In one example, the calculating may include comparing the words and/or phrases recorded to various profiles or signatures for different moods, e.g., where the profiles/signatures may comprise dictionaries or word lists that include words and/or phrases that are representative of the respective moods.

In still another example, biometric data gathered by device controller 190 for user 140 may include heart rate and breathing data. Thus, in one example, the mood of the user 140 may be determined based, at least in part, upon the heart rate data and/or breathing rate data. For instance, an elevated heart rate or breathing rate, e.g., as compared to a baseline/ resting rate for the user 140, may be indicative of duress, fear, anger, etc. It should be noted that different types of biometric data may be aggregated and matched to signatures/patterns for different moods that are comprised of multiple data points that account for the different types of biometric data. In one example, the mood/mental state of user 140 may be broadly classified as being a positive mood or a negative mood by quantifying the mental state/mood within a two or three dimensional space, e.g., according to an evaluative space model, a circumplex model, a vector model, a Positive Activation-Negative Activation (PANA) model, a Profile of Mood States (POMS), or the like.

For example, device controller 190 may quantify the extent to which user 140 matches various moods in accordance with biometric data that is gathered from various biometric sensors. For instance, a current image of user 140 may be quantized and evaluated to determine how closely the current image matches to eigenfaces of various moods (e.g., the respective distances in the feature space). In other words, the device controller 190 may not determine a single mood that best characterizes the current state of user 140, but may obtain a value for each mood that indicates how well the user 140 currently matches to the mood. In one example, the distance determined for each mood may be matched to a mood scale (e.g., "not at all", "a little bit", "moderately", "quite a lot", such as according to the POMS methodology). In addition, each level on the mood scale may be associated with a respective value (e.g., ranging from zero (0) for "not at all" to (4) for "quite a lot"). Next, the device controller 190 may determine an overall mental state score for user 140 in accordance with the values determined for various mental states. For example, the device controller 190 may sum values for negative moods/subscales and subtract this total from a sum of values for positive moods/subscales. Alternatively, or in addition, device controller 190 may calculate scores for certain subscales (e.g., tension, depression, anger, fatigue, confusion, vigor, or the like) comprising composites of different values for component mental states, wherein the score for one of the subscales may be considered as the mental state score of user 140, a composite of scores for two or more subscales may be considered the mental state score of user 140 (e.g., summing positive subscales, summing negative subscales, obtaining differences between one or more positive subscales and one or more negative subscales, such as a total mood disturbance (TMD)), and so forth.

In any case, the device controller 190 may quantify a mood of user 140 (e.g., a mental state score) as being "positive," "negative," or "neutral," or may grade the mood of user 140 on a numerical scale (e.g., 0 to 1, 0 to 100, −100 to +100, etc.). Device controller 190 may then determine that certain environmental conditions should be adjusted, e.g., via network connected devices 160, in response to certain (quantified) moods (e.g., negative moods, moods scored below a $30^{th}$ percentile on a scale of moods, etc.).

In one example, device 110 and/or server(s) 114 may also track or obtain data regarding the mood of user 140 and may adjust the user's preferences and tolerance ranges with regard to one or more environmental conditions and/or network connected device settings. For instance, when user 140 is observed to change from a positive mood to a negative mood for a particular device setting and with respect to a given "state," the tolerance range of user 140 may be adjusted up or down (e.g., depending upon whether a setting causing the negative mood is above or below what the user profile previous included as the preference range of user 140 for the device setting and/or the environmental condition). In one example, the device 110 and/or server(s) 114 may observe users moods over many different device settings and "states" and may use a regression analysis to identify correlations between device settings (predictors/independent variable) and the moods of user 140 (response/dependent variable) (e.g., over 6 months of historical data, a year of historical data, etc.), and adjust preferences and tolerance ranges in response to mood data over such longer time periods. For instance, device settings associated with negative moods may result in changes to preferences and/or tolerance ranges of user 140, while device settings associated with positive moods may result in "strengthening" or increased confidence of preferences and/or tolerance ranges. Thus, the user profile may adapt over time and may store effectiveness scores for various actions (e.g., changes/adjustments to network connected devices) with respect to improving moods of user 140.

For instance, in one example, the anticipated impact or effect of an automated action with respect to a mental state of user 140 may be determined based upon an effectiveness score for the automated action with respect to the mental state of the user 140. For instance, the effectiveness score may quantify the effectiveness of past implementations of various automated actions with respect to user 140 by comparing the mental state score of the user prior to an automated action to the mental state score of the user as determined after the implementation of the automated action. In one example, the effectiveness score may be based upon the magnitude of the change in the mental state score for the user 140. In addition, the effectiveness score may be aggregated and weighted over a number of past instances of the implementation of a same type of automated action for the user 140. Alternatively, or in addition, the effectiveness score may be aggregated and weighted over a number of past instances of the implementation of a same type of automated action for the user 140, and may further be segregated into scores for different times of day, or days of the week for which the automated action was implemented. For instance, in one example, device 110 and/or server(s) 114 may learn the effectiveness scores over various past trips of the user with regard to the user of various network connected devices of a same or similar type. In one example, the results of mental state score changes may be weighted to favor more recent results as compared to results from further in the past, e.g., an exponentially weighted moving average, etc. In addition, results from prior to a certain time may be excluded, e.g., only results from within the previous six months, from within the previous year, etc. may be used to calculate the effectiveness score.

As an example, in a past instance, the application of an automated action of dimming the lights via lighting system 162 may have resulted in a change of mental state score for user 140 from −20 to −18. However, in a same or a different instance, an automated action of adjusting the temperature from 75 degrees to 72 degrees may have resulted in a change of mental state score for user 140 from −19 to −5. Thus, the effectiveness score for the automated action of dropping the temperature may be greater for user 140 as compared to light dimming, e.g., an effectiveness score of 14 compared to an effectiveness score of 2. It should be noted that in one example, the effectiveness score may comprise a value representing the change in mental state score of a user. However, in another example, the effectiveness score may utilize a different scale and/or be weighted in a different manner where the effectiveness score does not directly correspond to the change in mental state score. For instance, the translation between change in mental state score and effectiveness score may not necessarily be linear. For example, a change in mental state score from −11 to −10 and a change in mental state score from −2 to −1 may correspond to different effectiveness scores according to a non-linear scaling (e.g., a scaling/weighting that is exponential, hyperbolic, parabolic, etc.).

In one example, when selecting an automated action with respect to user 140, the device controller 190 may select an automated action from among various available automated actions that the device controller 190 calculates will likely have a greatest anticipated impact (e.g., positively) with respect to the mental state of user 140, and based upon the types of the available network connected devices 160. In another example, the device controller 190 determine two or more settings of network connected devices 160 to adjust, where a combined effectiveness score may be anticipated to cause user 140 to change from an overall negative mood to a neutral or an overall positive mood. Alternatively, or in addition, the device controller 190 may select and implement a first action (e.g., an adjustment to a setting of at least one of the network connected devices 160), continue to gather biometric data and detect a mood of user 140, and determine that the first action did not result in an anticipated effect. For instance, the action may not have moved the user 140 away from an overall negative mood. In such case, the device controller 190 may then select one or more additional actions (e.g., another adjustment to a setting of at least one other of the network connected devices 160) in an attempt to further improve the mood of user 140.

It should be noted that in some examples, device controller 190 may more directly determine a negative physical condition of the user 140 and select an automated action (e.g., an adjustment to a setting of at least one of the network connected devices 160) accordingly. For instance, if the blood oxygen level of user 140 is determined to be low as determined from biometric data from a pulse oximeter, the device controller 190 may increase a percentage of oxygen in the air delivered via a fan to the seat 190. In addition, it should be noted that in any case, the user 140 may manually select settings for various network connected devices 160, which may override any settings automatically determined by device controller 190. In such case, the manual change made by user 140 may be recorded by device 110, which may use such data to change the user profile (such as changing the preferences and tolerance ranges for one or more settings and/or environmental conditions). Alternatively, or in addition, device 110 and/or device controller 190 may provide such information to server(s) 114, which may adjust the user profile in accordance with this information, and provide an updated user profile back to device 110 and/or other carrier computing systems for future trips of user 140.

In one example, an on-board computing device or portable computing device(s) of personnel of aircraft 170 may access mood data of user 140, other biometric data, and/or current settings of network connected devices 160, e.g., only with full consent and permission of user 140. In this way, aircraft personnel may better serve the passengers, including user 140. For instance, often passengers may complain that they are too hot or too thirsty, or claim a medical issue is occurring. Thus some passengers may simply be experiencing discomfort, whereas some passengers may be truly in need of assistance. Thus, aircraft personnel will be able to prioritize which passengers to attend to first, based upon which passenger appear to be actually experiencing negative physical conditions as evidenced by their biometric data, e.g., an excessive heart rate, a significant increase in body temperature, and the like.

In another example, one or more operations/functions described above with regard to device controller 190 may alternatively or additionally be performed by device 110. For instance, device controller 190 may enable device 110 to register to control network connected devices 160 in the personal zone 155 and to obtain biometric data from camera 166 and/or biometric sensors 167. Device 110 may therefore select initial settings for network connected devices 160, e.g., as described above, such as using midpoints of preferences ranges of user 140 regarding different network connected devices and/or environmental conditions. Device 110 may then obtain biometric data from camera 166 and/or biometric sensors 167, from any internal sensors, such as a microphone, and/or biometric sensor(s) 112, and may determine a physical condition of the user 140 and/or a mood of the user 140. In addition, device 110 may then determine one or more settings of one or more of network connected device 160 to adjust in response to the condition of the user (physical and/or mood) and in accordance with the user profile. In such case, in one example device controller 190 may receive instructions from device 110 and may pass the instructions to the respective network connected devices 160. In addition, device controller 190 may apply filters such that no setting is able to exceed an acceptable range as selected by the operator of aircraft 170 (e.g., where the network connected devices 160 may be capable of wider ranges, but are restricted by the operator of aircraft 170).

It should be noted that the foregoing describes just one illustrative scenario of how the system 100 may be used in connection with examples of the present disclosure for identifying at least one adjustment to at least one of a plurality of network-connected devices of a carrier transport vehicle in response to a condition of a user that is determined based upon biometric data obtained from at least one biometric sensor accessible via a mobile device of the user and a user profile. In addition, further details, such as example user interface aspects are illustrated in FIGS. 2 and 3.

It should also be noted that the system 100 has been simplified. Thus, the system 100 may be implemented in a different form than that which is illustrated in FIG. 1, or may be expanded by including additional endpoint devices, access networks, network elements, application servers, etc. without altering the scope of the present disclosure. In addition, system 100 may be altered to omit various elements, substitute elements for devices that perform the same or similar functions, combine elements that are illustrated as separate devices, and/or implement network elements as functions that are spread across several devices that operate collectively as the respective network elements. For example, the system 100 may include other network elements (not shown) such as border elements, routers, switches, policy servers, security devices, gateways, a content distribution network (CDN) and the like. For example, portions of network 102 and/or access networks 120 and 122 may comprise a content distribution network (CDN) having ingest servers, edge servers, and the like. Similarly, although only two access networks 120 and 122 are shown, in other examples, access networks 120 and/or 122 may each comprise a plurality of different access networks that may interface with network 102 independently or in a chained manner. For example, server 114 and gateway 181 may reach network 102 via different access networks, device 110 and biometric sensors 112 may reach network 102 via different access networks, and so forth. It should also be noted that although FIG. 1 and other examples herein are illustrated and described primarily in connection with passenger aircrafts, it should be noted that other, further, and different examples may similarly relate to trains, buses, ships, or other carrier transport vehicles. Thus, these and other modifications are all contemplated within the scope of the present disclosure.

Figure 2:
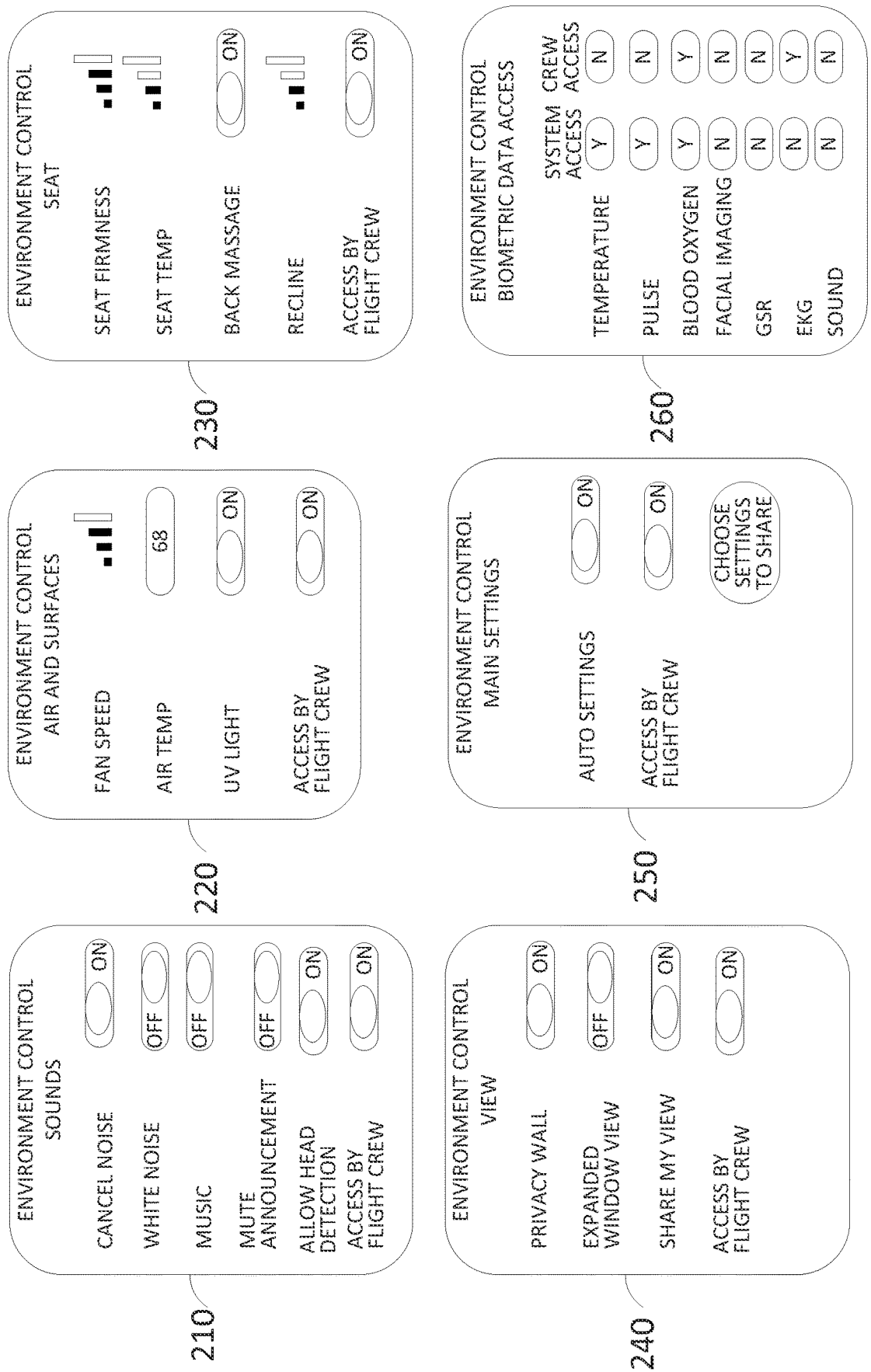
FIG. 2 illustrates example user interface screens of a user interface, in accordance with the present disclosure.

To further illustrate aspects of the present disclosure, FIG. 2 depicts example user interface screens 210-260 of a user interface related to the examples described herein. For instance, user interfaces screens 210-260 may be part of a personal environmental control application (app) provided by a carrier or other entities that may be utilized by a passenger (e.g., a user) via his or her mobile device or other computing devices. In the example of FIG. 2, the user interface screen 210 includes a variety of controls related to sound in a personal zone of a user (such as personal zone 155 of user 140 in FIG. 1). For instance, a user may be presented with on/off options for noise cancellation, white noise, music, and muting announcements. The user interface screen 210 may also include a permission setting relating to whether the user permits head detection via imaging, such as via an on-board camera of the carrier transport vehicle. In addition, user interface screen 210 may present a selection option for "access by flight crew." For instance, this setting may allow flight crew to access and view any of the above settings, e.g., via respective handheld devices of the flight crew or other on-board computing system(s).

In one example, a second user interface screen 220 may provide similar options regarding air quality and surfaces (e.g., surface sterilization treatment), such as: a fan speed setting, an air temperature setting, an ultraviolet (UV) light setting (e.g., a UV-C light for sterilization/sanitation, which is non-damaging to human skin), an "access by flight crew" option, and so forth. Still a third user interface screen 230 may provide environmental control options with regard to a user's seat, such as: seat firmness, seat temperature, a back massage on/off setting, a seat recline, and so forth. As in the preceding examples, user interface screen 230 may also include a selection option for "access by flight crew." A fourth example user interface screen 240 may include environmental control settings relating to a user's view, such as an on/off setting for a privacy wall, or screen, an expanded window view on/off setting, a "share my view" on/off setting, and a "share with flight crew" setting. With respect to the expanded window view, one or more display screens may provide an exterior window view which may simulate the user having a window seat, or in another example, as if there were no cabin wall. The "share my view" setting may grant or deny permission for the user to be included in other user's enhanced window views. For instance, the user may be omitted from another's user's expanded window view if this setting is set to "off."

Example user interface screen 250 illustrates an "auto settings" on/off setting, an "access by flight crew" setting. For instance, as noted above, examples of the present disclosure for identifying at least one adjustment to at least one of a plurality of network-connected devices of a carrier transport vehicle in response to a condition of a user that is determined based upon biometric data obtained from at least one biometric sensor accessible via a mobile device of the user and a user profile may be implemented by an on-board computing system or processing system, such as device controller 190 and/or by a user device, such as device 110. In other words, environmental control settings for various network connected devices may be automatically implemented in accordance with a user profile. Thus, for example, the automatic control may be activated and deactivated by the user via the "auto settings" on/off control.

A sixth example user interface screen 260 illustrates settings for user permissions regarding the accessibility of the user's biometric data, such as relating to temperature, pulse, blood oxygen level, facial image data, galvanic skin response (GSR) data, EKG data, sound data of the user, and so forth. For instance, for each type of biometric data the user may select whether or not the system may collect (or access) such data. For instance, in an example where operations are performed by a processing system of a carrier transport vehicle, the biometric data may still be gathered by a user's wearable computing device/biometric sensor, but not shared with the processing system of the carrier transport vehicle unless specifically authorized by the user. In fact, such biometric data may not even be allowed to be gathered from biometric sensors of the carrier transport vehicle unless specifically authorized by the user, even if available with respect to the personal zone of the user. It should be noted that some users may be comfortable to allow an automated system to optimize environmental settings based upon the user's biometric data, but may hesitate to share such data with other persons, such as flight crew. Thus, the permission settings for allowing or denying access to flight crew may be independent from the permission settings regarding access by an automated system.

It should be noted that the foregoing are just several example user interfaces that may be implemented in a user interface according to the present disclosure. For instance, the same or similar functionality may be provided via drop down menus, settings/controls may be grouped on different screens or menus, and so forth. In one example, the user interfaces may provide a user with the choice to share settings on a setting-by-setting basis, and so on. Thus, these and other modifications are all contemplated within the scope of the present disclosure.

FIG. 3 illustrates a flowchart of an example method 300 for identifying at least one adjustment to at least one of a plurality of network-connected devices of a carrier transport vehicle in response to a condition of a user that is determined based upon biometric data obtained from at least one biometric sensor accessible via a mobile device of the user and a user profile, in accordance with the present disclosure. In one example, the method 300 is performed by an on-board computing system, or processing system, of a carrier transport vehicle such as device controller 190 of FIG. 1, or any one or more components thereof, or by any such computing system/processing system in conjunction with other devices and/or components of system 100 of FIG. 1, e.g., server(s) 114, device 110, biometric sensor(s) 112, network connected devices 160, camera 166, biometric sensors 167, and so forth. In one example, the steps, functions, or operations of method 300 may be performed by a computing device or processing system, such as computing system 400 and/or hardware processor element 402 as described in connection with FIG. 4 below. For instance, the computing system 400 may represent any one or more components of the system 100 that is/are configured to perform the steps, functions and/or operations of the method 300. Similarly, in one example, the steps, functions, or operations of the method 300 may be performed by a processing system comprising one or more computing devices collectively configured to perform various steps, functions, and/or operations of the method 300. For instance, multiple instances of the computing system 400 may collectively function as a processing system. For illustrative purposes, the method 300 is described in greater detail below in connection with an example performed by a processing system. The method 300 begins in step 305 and proceeds to step 310.

At step 310, the processing system (e.g., of a carrier transport vehicle) establishes a wireless communication session with a mobile device of a user. In one example, the establishing the wireless communication session with the mobile device of the user comprises providing a control of at least a portion of a plurality of network-connected devices in the zone to the user via a user interface of the mobile device of the user.

At step 315, the processing system assigns a zone of the carrier transport vehicle to the user, the zone including a plurality of network-connected devices. For instance, the plurality of network-connected devices may include at least one biometric sensor of the zone of the carrier transport vehicle. As noted above, the at least one biometric sensor of the zone of the carrier transport vehicle may be deployed in an armrest of a seat of the user (or an overhead area immediately above the user's assigned seat, the back of the seat in front of the user's assigned seat, and the like). In this regard, the zone assigned to the user may be associated with a seat reserved/booked by the user for a journey via the carrier transport vehicle. The at least one biometric sensor of the zone may comprise at least one of: a thermal sensor, a pulse oximeter, a skin conductance sensor, a blood pressure meter, a pressure sensor, a microphone, a camera, and so forth.

At step 320, the processing system obtains a user profile from the mobile device of the user. For instance, as discussed above, the user profile may comprise preferences and tolerance ranges of the user regarding a plurality of environmental conditions. In one example, the user profile comprises a thermal preference model of the user. In one example, the user profile comprises mood profiles/models of the user. In one example, the use profile includes effectiveness scores for various automated actions, e.g., setting changes with respect to various network connected devices and/or environmental conditions.

At step 325, the processing system determines at least one biometric sensor accessible via the mobile device of the user. For instance, the at least one biometric sensor accessible via the mobile device of the user may comprise a microphone, a pulse oximeter, a hear rate monitor, a skin temperature sensor, and so forth. In one example, the at least one biometric sensor may be part of the mobile device of the user. Alternatively, or in addition, the at least one biometric sensor may comprise a separate wearable device that is in communication with the mobile device of the user.

At step 330, the processing system obtains biometric data of the user from the at least one biometric sensor accessible via the mobile device of the user, such as blood pressure, heart rate/pulse, skin temperature, EKG data, GSR data, and so forth. In one example, the biometric data of the user comprises at least one image of the user obtained via the camera. Alternatively, or in addition, in one example, the biometric data of the user may comprise acoustic/sound data, e.g., captured voice data of the user. For instance, the mobile device of the user may stream biometric data of the user to the processing system or may allow the processing system to access/retrieve the biometric data from the at least one biometric sensor.

At step 335, the processing system determines a condition of the user based upon the biometric data. For instance, the condition may comprise a physical condition (e.g., a skin temperature, a heartrate/pulse, a GSR measurement, an EKG pattern, a blood oxygen level, etc.) or a mood (e.g., irritated, content, anxious, nervous, angry, etc., such as a mood according to an evaluative space model, a circumplex model, a vector model, a Positive Activation-Negative Activation (PANA) model, a Profile of Mood States (POMS), or the like). In one example, the condition of the user comprises a first mood, wherein the determining the condition of the user based upon the biometric data is via at least one machine learning model for detecting the first mood in accordance with the biometric data as input features.

At step 340, the processing system identifies at least one adjustment to at least one of the plurality of network-connected devices in response to the condition of the user that is determined and the user profile. The at least one of the plurality of network connected devices that is adjusted may comprise at least one of: a humidistat (or humidifier), a thermostat, a fan, an oxygen source, a light source, a window shade, a privacy screen, and so forth. In one example, the identifying the at least one adjustment at step 340 may be based upon the condition of the user that is determined, the thermal preference model, and a temperature of the zone. In one example, the identifying the at least one adjustment may also be based on wind speed, or fan speed if there is no external detection of wind speed, or other factors, depending upon the particular configuration of the thermal preference model.

At step 345, the processing system applies the at least one adjustment to the at least one of the plurality of network-connected devices. For instance, the processing system may instruct a thermostat to adjust a temperature up or down, may instruct a fan to increase or decrease a fan speed, may instruct a seat to recline or return to an upright position, may instruct a window shade to open, close, or set itself halfway, may instruct a display screen to display video content from an exterior of the carrier transport vehicle, may instruct a lighting system to increase or decrease a light level and/or to change a color of light, may instruct a speaker to present music, a noise canceling signal, and so forth.

At optional step 350, the processing system may obtain a user input via the user interface of the mobile device of the user to adjust the at least one of the plurality of network-connected devices to a different setting from the at least one adjustment. For instance, the user may prefer a different setting than that which is selected by the processing system. For example, the user may have declined to share some biometric data, such that the processing system may have determined an inappropriate adjustment based upon less than all available information.

At optional step 355, the processing system may adjust the at least one of the plurality of network-connected devices to the different setting in accordance with the instruction, e.g., the user input. In other words, optional step 355 may carry out a manual override of the at least one adjustment to the at least one of the plurality of network-connected devices based on the user input.

At optional step 360, the processing system may detect that the user is in a different zone of the carrier transport vehicle. For instance, during the journey the user may move to different seats on a train or a bus, or may move to a lounge, a dining car, and so forth.

At optional step 365, the processing system may identify at least a second adjustment to at least one of a different plurality of network-connected devices in the different zone in response to the condition of the user that is determined and the user profile. For instance, optional step 365 may comprise the same or similar operations as step 340 above, or steps 330-340. In one example, optional step 365 may include determining the different plurality of network-connected devices in the different zone and associating the different plurality of network-connected devices with the user. In one embodiment, the processing system may also estimate the time that the user will likely be located at the different zone, e.g., whether the user is in line on the aisle of an aircraft waiting to use a bathroom, or whether the user is sitting in a dining car of a train. If the user is simply traversing thru a different zone momentarily (e.g., being on a line), the processing system may decline to make any adjustments in the different zone, whereas if the user is anticipated to be present at the different zone for an extended period (e.g., sitting in a dining car of a train), then the processing system may make the necessary adjustments as discussed above.

At optional step 370, the processing system may apply the at least the second adjustment to the at least one of the different plurality of network-connected devices. For instance, optional step 370 may comprise the same or similar operations as step 345 above.

Following step 345, or any of optional steps 350-370 the method 300 may proceed to step 395. At step 395 the method 300 ends.

It should be noted that the method 300 may be expanded to include additional steps, or may be modified to replace steps with different steps, to combine steps, to omit steps, to perform steps in a different order, and so forth. For instance, in one example the processing system may repeat one or more steps of the method 300, such as steps 325-345 for additional trips of the user on the same or a different type of carrier transport vehicle, and so on. In one example, the method 300 may include repeating steps 335-345 for continuous and/or ongoing monitoring of the condition of the user. For instance, the at least one adjustment determined at step 340 may be applied and may have an intended effect on the condition of the user. However, the biometric data of the user may subsequently reveal that the at least one adjustment did not achieve the intended effect on the condition of the user. Thus, for example, the processing system may determine at least one additional adjustment for a further attempt (and with an intended effect) to change the condition of the user (such as changing the user from a net negative mood to a net positive mood, changing the user from feeling hot or cold to "comfortable," or the like). In another example, the method 300 may be modified to be performed by a user device, e.g., a mobile device, such as device 110 of FIG. 1, or by such a user device in conjunction with other devices and/or components of system 100 of FIG. 1, e.g., device controller 190, etc. For example, at least a portion of the steps, functions, and/or operations of the method 300 may be performed by the user device. Thus, these and other modifications are all contemplated within the scope of the present disclosure.

In addition, although not expressly specified above, one or more steps of the method 300 may include a storing, displaying and/or outputting step as required for a particular application. In other words, any data, records, fields, and/or intermediate results discussed in the respective methods can be stored, displayed and/or outputted to another device as required for a particular application. Furthermore, operations, steps, or blocks in FIG. 3 that recite a determining operation or involve a decision do not necessarily require that both branches of the determining operation be practiced. In other words, one of the branches of the determining operation can be deemed as an optional step. Furthermore, operations, steps or blocks of the above described method(s) can be combined, separated, and/or performed in a different order from that described above, without departing from the example embodiments of the present disclosure.

FIG. 4 depicts a high-level block diagram of a computing system 400 (e.g., a computing device or processing system) specifically programmed to perform the functions described herein. For example, any one or more components or devices illustrated in FIG. 1, or described in connection with FIGS. 2-3, may be implemented as the computing system 400. As depicted in FIG. 4, the computing system 400 comprises a hardware processor element 402 (e.g., comprising one or more hardware processors, which may include one or more microprocessor(s), one or more central processing units (CPUs), and/or the like, where the hardware processor element 402 may also represent one example of a "processing system" as referred to herein), a memory 404, (e.g., random access memory (RAM), read only memory (ROM), a disk drive, an optical drive, a magnetic drive, and/or a Universal Serial Bus (USB) drive), a module 405 for identifying at least one adjustment to at least one of a plurality of network-connected devices of a carrier transport vehicle in response to a condition of a user that is determined based upon biometric data obtained from at least one biometric sensor accessible via a mobile device of the user and a user profile, and various input/output devices 406, e.g., a camera, a video camera, storage devices, including but not limited to, a tape drive, a floppy drive, a hard disk drive or a compact disk drive, a receiver, a transmitter, a speaker, a display, a speech synthesizer, an output port, and a user input device (such as a keyboard, a keypad, a mouse, and the like).

Although only one hardware processor element 402 is shown, the computing system 400 may employ a plurality of hardware processor elements. Furthermore, although only one computing device is shown in FIG. 4, if the method(s) as discussed above is implemented in a distributed or parallel manner for a particular illustrative example, e.g., the steps of the above method(s) or the entire method(s) are implemented across multiple or parallel computing devices, then the computing system 400 of FIG. 4 may represent each of those multiple or parallel computing devices. Furthermore, one or more hardware processor elements (e.g., hardware processor element 402) can be utilized in supporting a virtualized or shared computing environment. The virtualized computing environment may support one or more virtual machines which may be configured to operate as computers, servers, or other computing devices. In such virtualized virtual machines, hardware components such as hardware processors and computer-readable storage devices may be virtualized or logically represented. The hardware processor element 402 can also be configured or programmed to cause other devices to perform one or more operations as discussed above. In other words, the hardware processor element 402 may serve the function of a central controller directing other devices to perform the one or more operations as discussed above.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computing device, or any other hardware equivalents, e.g., computer-readable instructions pertaining to the method(s) discussed above can be used to configure one or more hardware processor elements to perform the steps, functions and/or operations of the above disclosed method(s). In one example, instructions and data for the present module 405 for identifying at least one adjustment to at least one of a plurality of network-connected devices of a carrier transport vehicle in response to a condition of a user that is determined based upon biometric data obtained from at least one biometric sensor accessible via a mobile device of the user and a user profile (e.g., a software program comprising computer-executable instructions) can be loaded into memory 404 and executed by hardware processor element 402 to implement the steps, functions or operations as discussed above in connection with the example method(s). Furthermore, when a hardware processor element executes instructions to perform operations, this could include the hardware processor element performing the operations directly and/or facilitating, directing, or cooperating with one or more additional hardware devices or components (e.g., a co-processor and the like) to perform the operations.

The processor (e.g., hardware processor element 402) executing the computer-readable instructions relating to the above described method(s) can be perceived as a programmed processor or a specialized processor. As such, the present module 405 for identifying at least one adjustment to at least one of a plurality of network-connected devices of a carrier transport vehicle in response to a condition of a user that is determined based upon biometric data obtained from at least one biometric sensor accessible via a mobile device of the user and a user profile (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium may comprise a physical device, a hardware device, or a device that is discernible by the touch. More specifically, the computer-readable storage device or medium may comprise any physical devices that provide the ability to store information such as instructions and/or data to be accessed by a processor or a computing device such as a computer or an application server.

While various examples have been described above, it should be understood that they have been presented by way of example only, and not limitation. Thus, the breadth and scope of a preferred example should not be limited by any of the above-described examples, but should be defined only in accordance with the following claims and their equivalents.

What is claimed is:

1. An apparatus comprising:
a processing system including at least one processor; and
a computer-readable medium storing instruction that, when executed by the processing system when deployed in a carrier transport vehicle, cause the processing system to perform operations, the operations comprising:
establishing a wireless communication session with a mobile device of a user;
assigning a zone of the carrier transport vehicle to the user, the zone including a plurality of network-connected devices, wherein the plurality of network-connected devices includes at least one biometric sensor of the zone of the carrier transport vehicle, wherein the at least one biometric sensor of the zone of the carrier transport vehicle comprises a camera;
obtaining a user profile from the mobile device of the user, wherein the user profile comprises a thermal preference model of the user;
determining at least one biometric sensor accessible via the mobile device of the user;
obtaining biometric data of the user from the at least one biometric sensor accessible via the mobile device of the user and from the at least one biometric sensor of the zone of the carrier transport vehicle, wherein the biometric data of the user comprises at least one image of a face of the user obtained via the camera;
determining a condition of the user based upon the biometric data, wherein the condition of the user comprises a first mood, wherein the determining the condition of the user based upon the biometric data is via at least one machine learning model for detecting the first mood in accordance with the biometric data comprising the at least one image of the face of user as input features;
identifying at least one adjustment to at least one of the plurality of network-connected devices in response to the condition of the user that is determined and the user profile, wherein the identifying the at least one adjustment is based upon an output of the thermal preference model, wherein the thermal preference model is configured to generate the output comprising a comfort level of the user based upon a plurality of inputs comprising: the condition of the user that is determined and a temperature of the zone; and
applying the at least one adjustment to the at least one of the plurality of network-connected devices to change at least one environmental condition of the zone, wherein the at least one of the plurality of network-connected devices that is adjusted comprises at least one of: a humidistat, a thermostat, a fan, an oxygen source, a light source, a window shade, or a privacy screen.

2. The apparatus of claim 1, wherein the at least one biometric sensor of the zone of the carrier transport vehicle is deployed in an armrest of a seat assigned to the user.

3. The apparatus of claim 1, wherein the at least one biometric sensor of the zone further comprises at least one of:
a thermal sensor;
a pulse oximeter;
a skin conductance sensor;
a blood pressure meter;
a pressure sensor; or
a microphone.

4. The apparatus of claim 1, wherein the user profile comprises preferences and tolerance ranges of the user regarding a plurality of environmental conditions.

5. The apparatus of claim 4, wherein the identifying the at least one adjustment is based upon the condition of the user that is determined, the user profile, and at least one environmental condition of the zone.

6. The apparatus of claim 5, wherein the plurality of network-connected devices includes at least one environmental sensor, and wherein the at least one environmental condition of the zone is determined via the at least one environmental sensor.

7. The apparatus of claim 6, wherein the at least one environmental sensor comprises at least one of:
a thermal sensor;
a light sensor;
a microphone;
a humidity sensor;
a particulate matter detector; or
an oxygen sensor.

8. The apparatus of claim 1, wherein the establishing the wireless communication session with the mobile device of the user comprises providing a control of at least a portion of the plurality of network-connected devices in the zone to the user via a user interface of the mobile device of the user.

9. The apparatus of claim 8, wherein the operations further comprise:
obtaining a user input via the user interface of the mobile device of the user to adjust the at least one of the plurality of network-connected devices to a second setting that is different from a first setting that results from the applying of the at least one adjustment; and
adjusting the at least one of the plurality of network-connected devices to the second setting in accordance with the user input.

10. The apparatus of claim 9, wherein the operations further comprise:
updating the user profile in accordance with the second setting.

11. The apparatus of claim 1, wherein the operations further comprise:
detecting that the user is in a different zone of the carrier transport vehicle;
identifying at least a second adjustment to at least one of a different plurality of network-connected devices in the different zone in response to the condition of the user that is determined and the user profile; and
applying the at least the second adjustment to the at least one of the different plurality of network-connected devices.

12. A non-transitory computer-readable medium storing instructions that, when executed by a processing system including at least one processor, cause the processing system to perform operations when deployed in a carrier transport vehicle, the operations comprising:
establishing a wireless communication session with a mobile device of a user;
assigning a zone of the carrier transport vehicle to the user, the zone including a plurality of network-connected devices, wherein the plurality of network-connected devices includes at least one biometric sensor of the zone of the carrier transport vehicle, wherein the at least one biometric sensor of the zone of the carrier transport vehicle comprises a camera;
obtaining a user profile from the mobile device of the user, wherein the user profile comprises a thermal preference model of the user;
determining at least one biometric sensor accessible via the mobile device of the user;
obtaining biometric data of the user from the at least one biometric sensor accessible via the mobile device of the user and from the at least one biometric sensor of the zone of the carrier transport vehicle, wherein the biometric data of the user comprises at least one image of a face of the user obtained via the camera;
determining a condition of the user based upon the biometric data, wherein the condition of the user comprises a first mood, wherein the determining the condition of the user based upon the biometric data is via at least one machine learning model for detecting the first mood in accordance with the biometric data comprising the at least one image of the face of the user as input features;
identifying at least one adjustment to at least one of the plurality of network-connected devices in response to the condition of the user that is determined and the user profile, wherein the identifying the at least one adjustment is based upon an output of the thermal preference model, wherein the thermal preference model is configured to generate the output comprising a comfort level of the user based upon a plurality of inputs comprising: the condition of the user that is determined and a temperature of the zone; and
applying the at least one adjustment to the at least one of the plurality of network-connected devices to change at least one environmental condition of the zone, wherein the at least one of the plurality of network-connected devices that is adjusted comprises at least one of: a humidistat, a thermostat, a fan, an oxygen source, a light source, a window shade, or a privacy screen.

13. A method comprising:
establishing, by a processing system including at least one processor deployed in a carrier transport vehicle, a wireless communication session with a mobile device of a user;
assigning, by the processing system, a zone of the carrier transport vehicle to the user, the zone including a plurality of network-connected devices, wherein the plurality of network-connected devices includes at least one biometric sensor of the zone of the carrier transport vehicle, wherein the at least one biometric sensor of the zone of the carrier transport vehicle comprises a camera;
obtaining, by the processing system, a user profile from the mobile device of the user, wherein the user profile comprises a thermal preference model of the user;
determining, by the processing system, at least one biometric sensor accessible via the mobile device of the user;
obtaining, by the processing system, biometric data of the user from the at least one biometric sensor accessible via the mobile device of the user and from the at least one biometric sensor of the zone of the carrier transport vehicle, wherein the biometric data of the user comprises at least one image of a face of the user obtained via the camera;
determining, by the processing system, a condition of the user based upon the biometric data, wherein the condition of the user comprises a first mood, wherein the determining the condition of the user based upon the biometric data is via at least one machine learning model for detecting the first mood in accordance with the biometric data comprising the at least one image of the face of the user as input features;
identifying, by the processing system, at least one adjustment to at least one of the plurality of network-connected devices in response to the condition of the user that is determined and the user profile, wherein the identifying the at least one adjustment is based upon an output of the thermal preference model, wherein the thermal preference model is configured to generate the output comprising a comfort level of the user based upon a plurality of inputs comprising: the condition of the user that is determined and a temperature of the zone; and
applying, by the processing system, the at least one adjustment to the at least one of the plurality of network-connected devices to change at least one environmental condition of the zone, wherein the at least one of the plurality of network-connected devices that is adjusted comprises at least one of: a humidistat, a thermostat, a fan, an oxygen source, a light source, a window shade, or a privacy screen.

14. The method of claim 13, wherein the at least one biometric sensor of the zone of the carrier transport vehicle is deployed in an armrest of a seat assigned to the user.

15. The method of claim 13, wherein the at least one biometric sensor of the zone further comprises at least one of:
- a thermal sensor;
- a pulse oximeter;
- a skin conductance sensor;
- a blood pressure meter;
- a pressure sensor; or
- a microphone.

16. The method of claim 13, wherein the user profile comprises preferences and tolerance ranges of the user regarding a plurality of environmental conditions.

17. The method of claim 16, wherein the identifying the at least one adjustment is based upon the condition of the user that is determined, the user profile, and at least one environmental condition of the zone.

18. The method of claim 17, wherein the plurality of network-connected devices includes at least one environmental sensor, and wherein the at least one environmental condition of the zone is determined via the at least one environmental sensor.

19. The method of claim 18, wherein the at least one environmental sensor comprises at least one of:
- a thermal sensor;
- a light sensor;
- a microphone;
- a humidity sensor;
- a particulate matter detector; or
- an oxygen sensor.

20. The method of claim 18, wherein the establishing the wireless communication session with the mobile device of the user comprises providing a control of at least a portion of the plurality of network-connected devices in the zone to the user via a user interface of the mobile device of the user.

* * * * *